United States Patent [19]

Onodera

[11] Patent Number: 5,074,334
[45] Date of Patent: Dec. 24, 1991

[54] MULTI-WAY COCK

[75] Inventor: Tsuneyoshi Onodera, Yamanashi, Japan

[73] Assignee: Terumo Kabushiki Kaisha, Tokyo, Japan

[21] Appl. No.: 558,493

[22] Filed: Jul. 27, 1990

[30] Foreign Application Priority Data

Jul. 27, 1989 [JP] Japan .................................. 1-195338

[51] Int. Cl.[5] .............................................. A61M 1/00
[52] U.S. Cl. .................................. 137/625.41; 604/32; 604/248
[58] Field of Search ............... 604/248, 246, 32, 35, 604/27; 137/625.41, 625.46, 625.47

[56] References Cited

U.S. PATENT DOCUMENTS

| 3,057,370 | 10/1962 | Hamilton | 137/625.47 |
| 3,185,179 | 5/1961 | Harautuneian | 137/625.47 |
| 3,750,704 | 8/1973 | Burke et al. | 137/625.47 |
| 4,593,717 | 6/1986 | Levasseur | 137/625.47 |
| 4,790,193 | 12/1988 | Moriuchi et al. | 137/625.47 |
| 4,816,339 | 3/1989 | Tu et al. | 623/11 |
| 4,834,037 | 5/1989 | Lafever | 277/189 |
| 4,900,322 | 2/1990 | Adams | 604/248 |
| 4,904,245 | 2/1990 | Chen et al. | 604/248 |

FOREIGN PATENT DOCUMENTS 59-197456 11/1984 Japan .

Primary Examiner—C. Fred Rosenbaum
Assistant Examiner—Mark Bockelman
Attorney, Agent, or Firm—Burns, Doane, Swecker & Mathis

[57] ABSTRACT

A multi-way cock comprises a housing including a cylinder having a plurality of branch tubes extending from the periphery thereof, and a plug including a barrel adapted to be rotatably fitted in the cylinder and having a corresponding plurality of channels formed therein, the channels corresponding to the branch tubes in assembled condition. The barrel is formed of a polyester elastomer.

7 Claims, 4 Drawing Sheets

MULTI-WAY COCK

This invention relates to multi-way cocks, typically three-way cocks for changing over flow paths of fluids such as blood and medicament fluid.

BACKGROUND OF THE INVENTION

In the medical field, multi-way cocks, typically three-way cocks are widely used for various purposes including transfusion of blood and infusion of fluid medicaments such as glucose fluid and physiological saline to patients. Infusion systems often use a plurality of fluid medicaments which should be kept separate until infusion. A three-way cock involved in the system is manipulated such that selected fluid medicaments may be either separately or simultaneously infused into the patient. Also in blood transfusion systems, three-way cocks are often useful in introducing a desired medicament into transfusing blood or in alternating blood transfusion and fluid infusion.

In general, the three-way cocks are composed of a housing including a cylinder having three T-shaped branch tubes extending from the periphery thereof. A plug is combined with the housing, which includes a barrel adapted to be rotatably fitted in the cylinder and having three T-shaped channels corresponding to the branch tubes. A manual lever is attached to the top of the plug barrel for rotating the plug in the cylinder. By manipulating the lever, the plug can be rotated over an angle of 180 degrees with respect to the housing. When the lever is at one of angular positions, two of the three branch tubes are selectively brought in fluid communication through corresponding channels in the plug barrel while the remaining branch tube is shut off from communication. The cock assembly in which the plug is snugly fitted in the housing is required to be highly tight against fluid under pressure and durable in that such high fluid tightness is maintained over a number of plug changeovers (for example, 200 cycles of back-and-forth rotation).

Conventional three-way cocks generally have housings formed of rigid resin materials such as polycarbonate. For the plug, more particularly its barrel, high density polyethylene is often used because of biological compatibility, workability, and low cost. With this combination, however, the housing material is rather less compatible with the plug material, and the plug barrel is susceptible to failure as by scraping and abrasion when the plug is fitted in the housing or when the plug is rotated during service. Such failure often occurs at or near the edge of the openings that the channels define at the outer surface of the barrel.

In recent years, the development of three-way cocks accommodating an increased flow rate is desired in order to accelerate blood and fluid infusion processes. To this end, the channels in the plug barrel should be enlarged to a larger diameter than the currently used one. If the channel diameter, that is, the diameter of the opening that the channel defines at the barrel outer surface is increased, the circumference of the opening is accordingly increased, resulting in increased chances of failure. Since the three-way cock is designed such that a pressure resistant fluid tight seal is established by close engagement of the housing cylinder's inner surface with the plug barrel's outer surface in assembled condition, a failure will leave a gap in the engagement, resulting in a loss of fluid tight seal. In addition, if chips or fragments are produced by chipping or scraping, such fragments can be conveyed into the blood or fluid to be infused, imposing potential damage to the patient. The use of such three-way cocks is not recommended in the medical field.

Therefore, an object of the present invention is to provide a novel and improved multi-way cock in which the plug barrel can be formed with larger diameter channels than in the prior art and is fully resistant to damage as by scraping and abrasion upon insertion of the plug into the housing or during the heavy duty service.

SUMMARY OF THE INVENTION

Investigating the material of which the plug is formed, the inventors have found that polyester elastomers are advantageous in that the plug barrel formed thereof is not susceptible to damage by scraping and abrasion particularly at or near the edge of the opening the channels define at the barrel outer surface even when the channels are formed to an increased diameter as compared with conventional ones.

The present invention is directed to a multi-way cock comprising a housing including a cylindrical portion having a plurality of branch tubes extending from the outer periphery thereof; and a plug including a barrel adapted to be rotatably fitted in the cylindrical portion and having a corresponding plurality of channels formed therein, the channels corresponding to the branch tubes in assembled condition. According to the feature of the invention, the barrel is formed of a polyester elastomer.

Preferably, the polyester elastomer has a modulus in flexure of at least 800 kgf/cm². The polyester elastomer is typically a polyether polyester elastomer which has a structure of the formula:

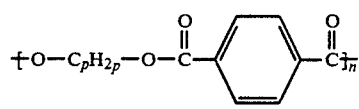

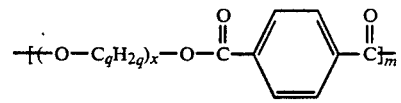

wherein n is a number of from 1 to 50, m is a number of from 1 to 5, p is a number of from 1 to 8, q is a number of from 1 to 8, and x is a number of from 5 to 50. In turn, the housing is formed of a rigid resin.

The openings that the channels define at the outer periphery of the barrel can have a diameter of 1.5 to 5 mm. The plug includes a lever for turning the plug in the housing, and the outer surface of the lever is entirely or partially coated with a resin which is visually different from the barrel-forming elastomer.

The cock is typically a two or three-way cock and often used in the medical field.

BRIEF DESCRIPTION OF THE DRAWINGS

The above and other objects, features, and advantages of the present invention will be better understood from the following description taken in conjunction with the accompanying drawings, in which.

Like parts are designated by the same reference numerals throughout the figures.

DESCRIPTION OF THE PREFERRED EMBODIMENTS

Figure 1:
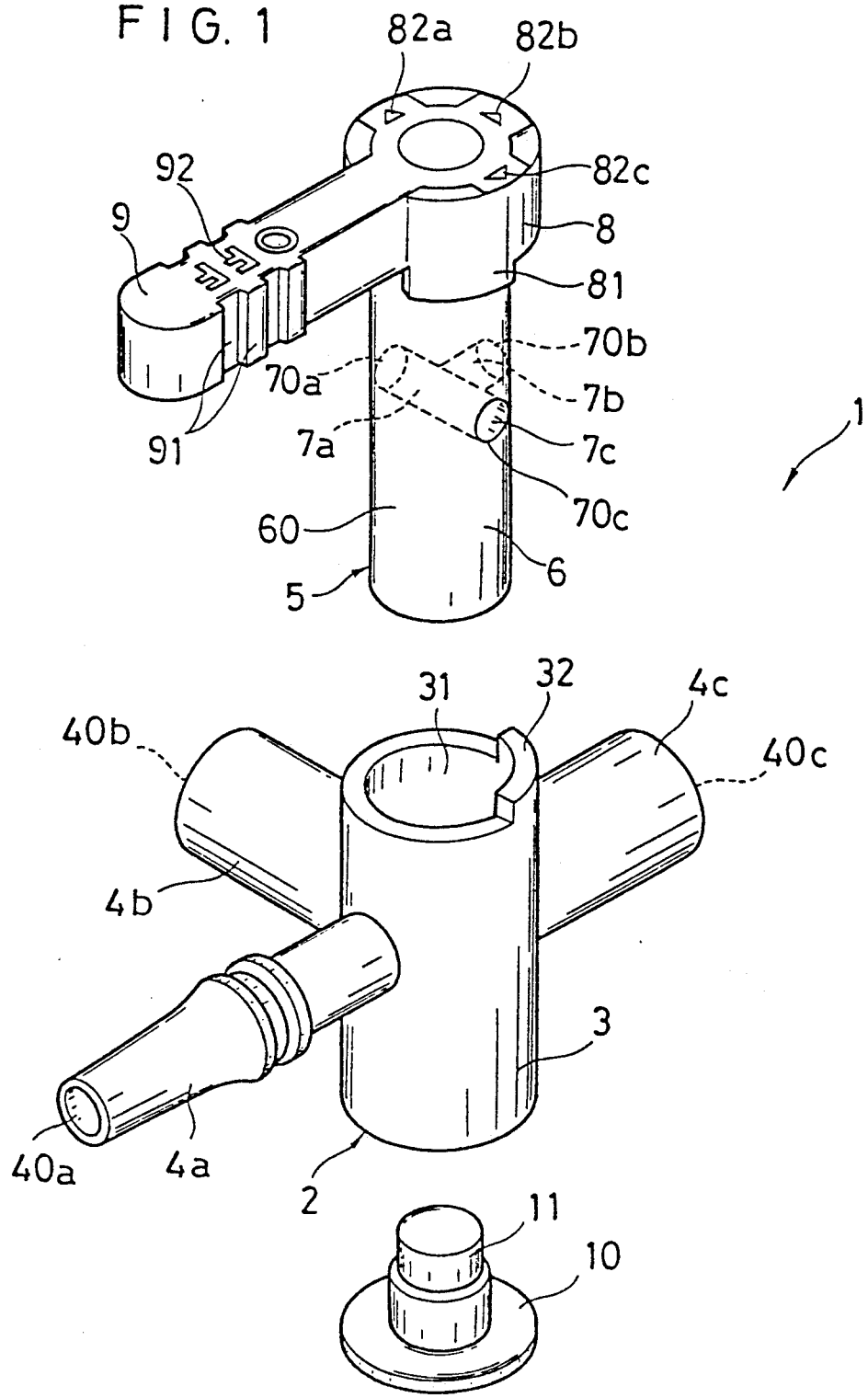
FIG. 1 is a perspective view showing a multi-way cock with its components disassembled according to one embodiment of the present invention.
Figure 2:
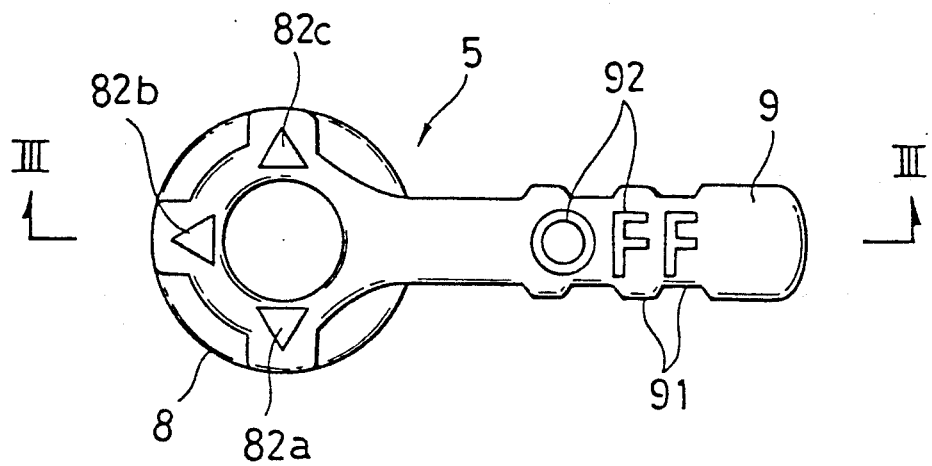
FIG. 2 is a plan view of the plug in the multi-way cock shown in FIG. 1.
Figure 3:
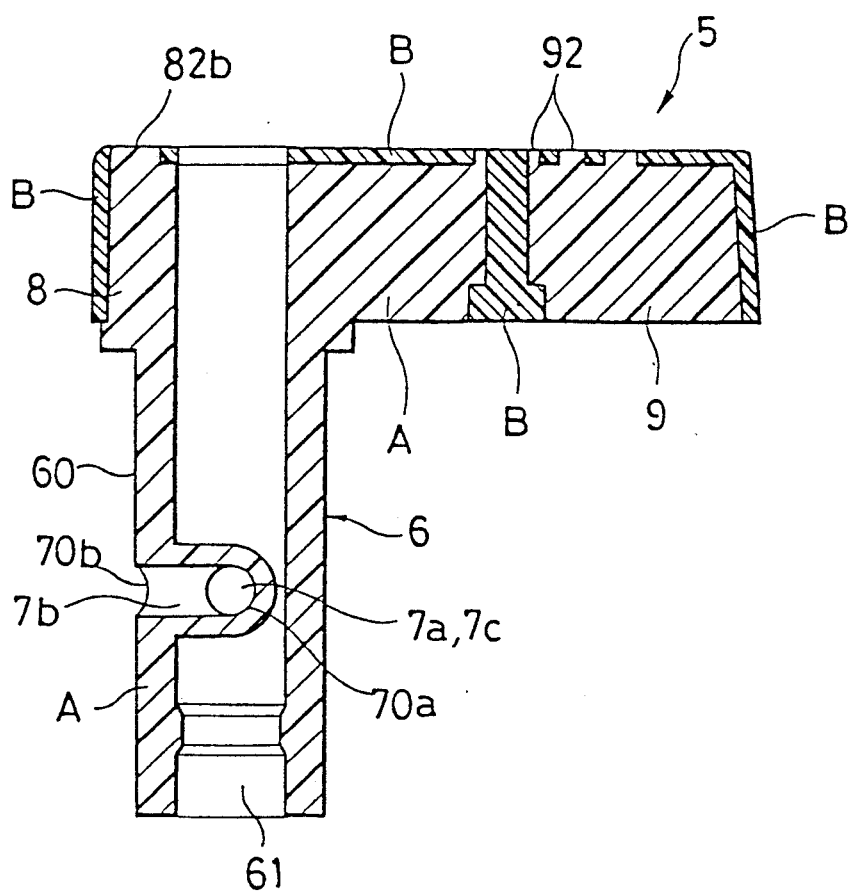
FIG. 3 is a cross sectional view of the plug taken along lines III—III in FIG. 2.
Figure 4:
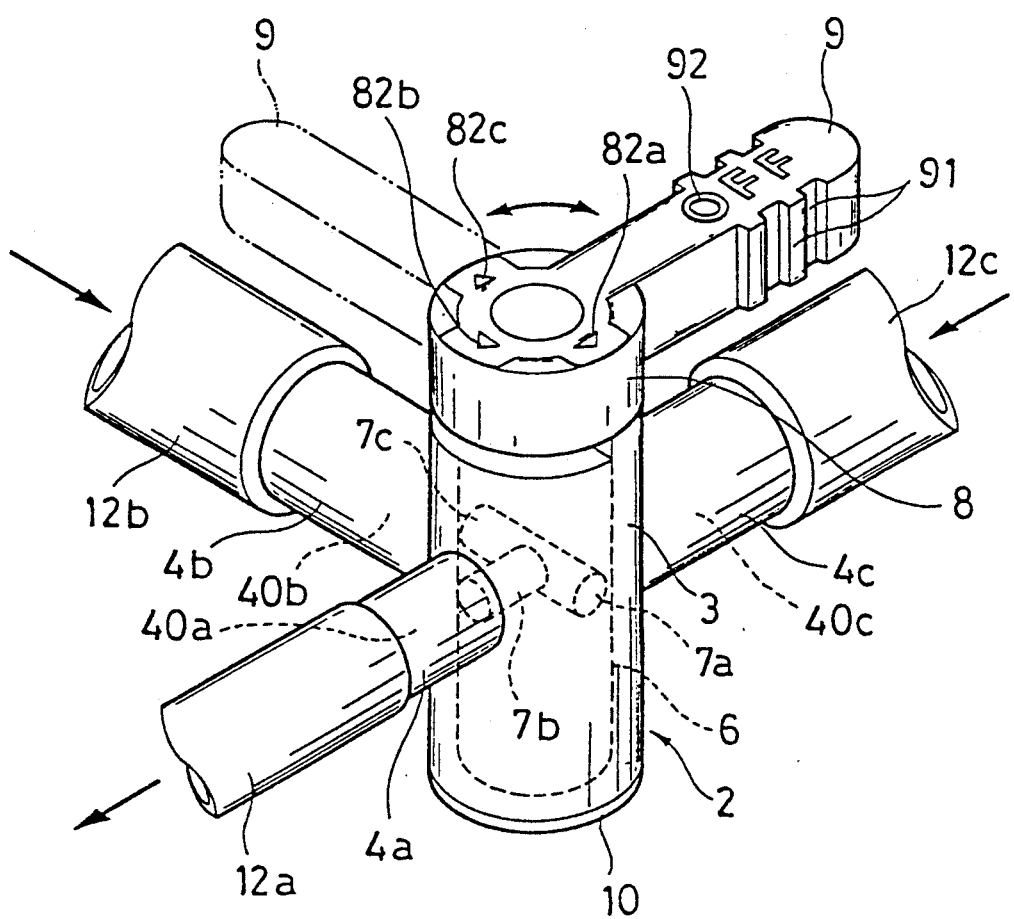
FIG. 4 is a perspective view of the multi-way cock of FIG. 1 in assembled form, showing its operation.

Referring to FIGS. 1 through 4, there is illustrated a multi-way cock according to one embodiment of the present invention. More particularly, a three way cock is illustrated in FIG. 1 as a typical example with its components disassembled. The cock in full assembly is illustrated in FIG. 4. The multi-way cock generally designated at 1 comprises a housing 2, a plug 5, and a lid 10.

The housing or holder 2 includes a hollow cylindrical portion 3 defining a bore 31 therein. The cylindrical portion 3 typically has an inner diameter of about 5 to about 8 mm and a wall thickness of about 1 to about 1.5 mm although these dimensions are not critical. Three branches 4a, 4b and 4c are spaced 90 degrees around the outer periphery and extended radially outward from the outer periphery of the cylindrical portion 3. The branches 4a and 4c are on a straight line and the branch 4b intersects the line at right angles in the illustrated embodiment. Preferably, the branches 4a, 4b and 4c are integrally formed with the cylindrical portion 3. The branches 4a, 4b and 4c define channels 40a, 40b and 40c therein, respectively, which communicate with the bore 31. The branches 4a, 4b and 4c typically have an inner diameter of about 1.5 to about 3.0 mm although the inner diameter is not critical. The cylindrical portion 3 further has a stationary restrainer 32 which is an arcuate segment extending axially upward from the upper edge of cylindrical portion 3.

The plug 5 includes a barrel 6, a lever support 8, and a lever 9 as shown in FIGS. 1 to 3. The barrel 6 is either a solid or hollow cylinder (solid in FIG. 1, but hollow in FIG. 3) and adapted to be rotatably fitted in the bore 31 of cylindrical portion 3 in a fluid seal manner. Prior to assembly, the plug barrel 6 preferably has an outer diameter which is approximately 2 to 5% larger than the inner diameter of the cylindrical portion 3. The barrel 6 should have a smooth outer surface 60, typically with a surface roughness (Rmax) of about 0.001 mm or less.

In the barrel 6, three channels 7a, 7b and 7c are defined in a T shape in correspondence with the channels 40a, 40b and 40c in the branches, respectively. Three channels 7a, 7b and 7c are spaced 90 degrees and extended radially from the axis of the barrel 6 so that they join together for fluid communication at the barrel center. The channels 7a and 7c are on a straight line and the channel 7b intersects the line at right angles in the illustrated embodiment. The channels 7a, 7b and 7c are also located at an axial height such that they mate with the channels 40a, 40b and 40c in the branches, respectively, when the plug 5 is fitted in the housing 2, that is, in the assembled cock.

The channels 7a-7c open at the barrel outer surface 60 to define circular openings 70a-70c. The openings 70a-70c (channels 7a-7c) typically have a diameter of about 1.5 to about 2.0 mm as in the conventional three-way cock design, but may have a larger diameter of about 2 to about 5 mm, especially 2.0 to 3.0 mm although the diameter is not critical. According to the invention, the barrel 6 is formed of a polyester elastomer, as will be described later in detail, which withstands chipping as by abrasion even when the openings 70a-70c have a larger diameter of about 2 to about 5 mm. Typically, the diameter of openings 70a-70c is substantially equal to that of channels 7a-7c. The larger the diameter of openings 70a-70c, the greater becomes the flow rate. Further, the openings 70a-70c most often have an equal diameter although they may have different diameters. Preferably, the edge of the openings 70a-70c is chamfered for enhanced protection of the edge and surrounding portion against chipping.

On top of the barrel 6 is provided, preferably integrally formed, the lever support 8 of generally cylindrical shape having a somewhat larger diameter than the barrel. The lever support 8 is adapted to be exposed above the assembled cock.

The support 8 at a lower end has a rotating restrainer 81 which is an arcuate segment extending axially downward from the outer wall of the support 8. In the assembled cock, as the plug 5 is rotated relative to the housing 2, the rotating restrainer 81 on support 8 engages the stationary restrainer 32 on cylindrical portion 3 to restrain rotation of the plug 5 within a predetermined angular range. Assume that the included angles of the stationary restrainer 32 and rotating restrainer 81 sum to 180° C., the plug 5 is allowed for rotation over an angle of 360° C. minus 180° C., that is, 180° C. It will be understood that the stationary restrainer 32 and rotating restrainer 81 are not essential to the invention. The plug 5 is allowed for free rotation over 360 degrees if any restraint means is absent.

The lever 9 extends from the lever support 8 in an opposite direction to the barrel channel 7b. Preferably the lever 9 is integrally formed with the support 8. The lever 9 near the free end is provided with anti-slip recesses 91. The plug 5 may be rotated relative to the housing 2 by gripping the lever with fingers to apply torque thereto.

It is to be noted that all the channels 40a-40c in the branches 4a-4c are commonly in flow communication when the lever 9 is turned opposite to the branch 4b.

The lever for rotating the plug is not limited to a unidirectional lever as illustrated. For example, two or more radial legs extending from the support or a wheel mounted on the support may be used.

On the top surface of the lever support 8, there are provided arrow marks 82a, 82b and 82c indicating the direction of respective barrel channels 7a, 7b and 7c of the plug 5. Also, the lever 9 bears an appropriate indication 92 on the top. Since the lever is positioned relative to the barrel channels 7a-7c such that one of the branch channels 40a-40c which comes in register with the lever 9 is closed, the indication 92 should preferably have such a meaning. Characters "OFF" is used in the illustrated example. The marks 82 and indication 92 may be formed by any desired techniques including paint drawing, printing, stickers or inscription.

In one embodiment, the marks 82 and indication 92 are uniquely formed as best shown in FIG. 3. The lever support 8 and lever 9 (more exactly their base member)

is formed of a first material designated A in the figure and covered with a second material designated B in the figure over the entire outer surfaces except those areas corresponding to the marks 82 and indication 92. In some areas like an area near the center of the lever in FIG. 3, an inner recess in the first material is filled with the second material B. It suffices that the first and second materials A and B are different in color and brightness. Then the marks 82 and indication 92 are exposed distinct from the remaining cover surface. Materials A and B may be integrated by adhesive bonding or fusion welding, but integral forming by multi-color (two-color) molding or mold shaping is preferred for structural rigidity.

The lid 10 is a disk member having a central stub 11 extending axially therefrom. The lid 10 is adapted to fit in the bottom of the cylindrical portion 3 of housing 2 to sealingly close the bore 31 at one end, that is, the bottom end in the illustrated embodiment. When the lid 10 is attached to the housing 2 to complete a cock, the lid stub 11 is received in a recess or opening 61 which is defined at the lower end of the barrel 6 as shown in FIG. 3.

Although the three-way cock has been described as a typical example, the cock may be provided with four or more branches extending in four or more directions if desired.

Figure 5:
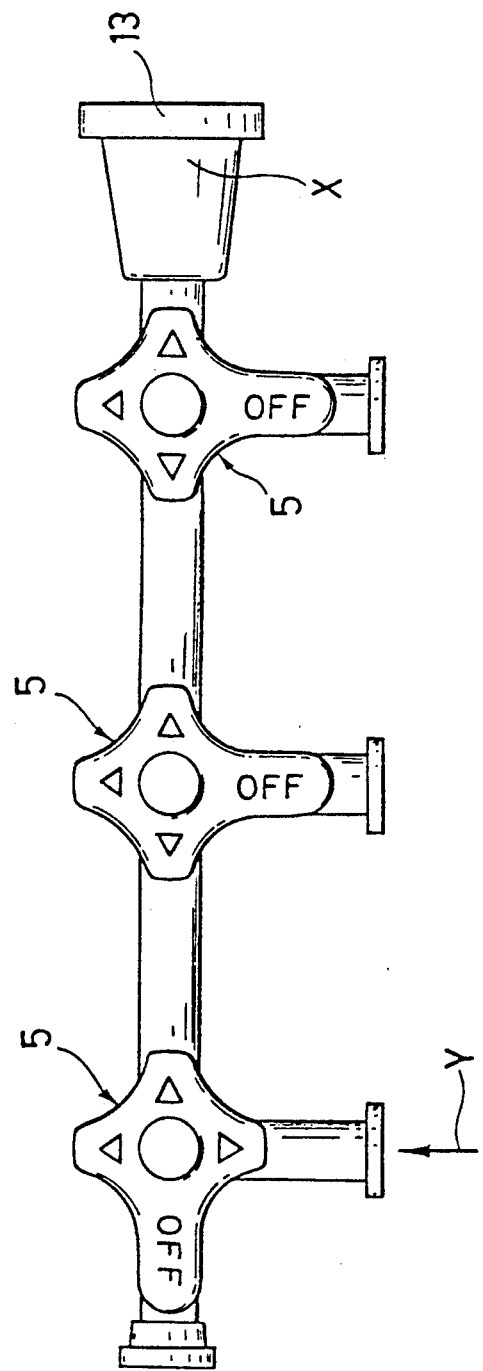
FIG. 5 is a plan view of a series of multi-way cocks used in an experiment.

It is also contemplated herein to couple a plurality of three-way cocks having the above-mentioned construction through any suitably selected branches to form an ensemble of cocks as shown in FIG. 5.

Next, the materials of which respective components of the three-way cock are made are described.

The housing 2 is generally formed of rigid materials such as metals and rigid resins to provide necessary rigidity although rigid resins are preferred for several reasons including ease of molding. Such rigid resins include polycarbonates, polyamides, and the like. Preferably, the housing materials have a modulus in flexure of about 20,000 to about 30,000 kgf/cm². Use of transparent material is advantageous for a view through the housing 2.

The plug 5, particularly its barrel 6, more particularly material A in FIG. 3, is formed of a polyester elastomer. A variety of polyester elastomers may be used while polyether polyester elastomers are preferred.

The preferred polyether polyester elastomers have a structure of the formula:

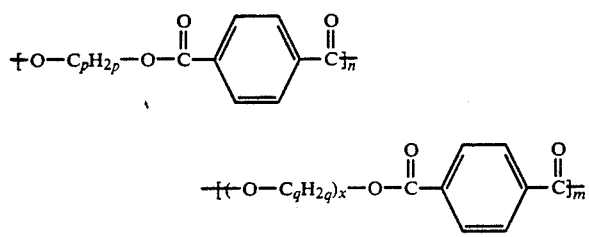

wherein
n is a number of from 1 to 50, especially 2 to 30,
m is a number of from 1 to 5,
p is a number of from 1 to 8,
q is a number of from 1 to 8, and
x is a number of from 5 to 50, especially 10 to 30.
The elastomers of the formula wherein n is 2 to 30, m is 1, p is 3, q is 4, and x is 10 to 30 are commercially available as Perprene ® (manufactured and sold by Toyobo K. K.).

The use of such elastomers as the plug 5 or barrel 6 is effective in preventing chipping or any failure of the barrel by scraping, abrasion, and other frictional actions caused when the plug 5 is inserted into the housing 2 and when the plug 5 is rotated therein during cock operation. In addition, the elastomers have high biological affinity and are free of dissolving-out toxic substances, and are least susceptible to thrombus adhesion when the cock is used for blood transfusion.

The polyester elastomers as typified by Perprene have widely varying physical properties. Preferably, they have a modulus in flexure of at least 800 kgf/cm², more preferably at least 1,000 kgf/cm², further preferably at least 1,200 kgf/cm², and most preferably at least 3,000 kgf/cm². The upper limit is usually 15,000 kgf/cm². A modulus in flexure of at least 800 kgf/cm² ensures that any failures like chipping do not occur, irrespective of the identity of the housing 2 (including its material and hardness) and the diameter of the openings 70a–70c being enlarged to 2.0 to 3.0 mm or larger. Below this lower limit, the barrel can be deformed under pressure to allow leakage though no scraping occurs.

For similar reasons, the polyester elastomers preferably have a surface hardness of about 95 to 100 as measured in Shore A hardness according to JIS K-6301.

The second material B used as a surface cover of the plug 5 as shown in FIG. 3 is not particularly limited because they serve no substantial function. For firm bonding to the base material A, the cover material B should preferably be of the same type as material A, that is, contain a major proportion of a polyester elastomer. No limitations regarding modulus and hardness are imposed to cover material B. The cover material B preferably contains a pigment for coloring purpose because it should be distinguished in color, brightness or appearance from base material A.

The lid 10 may be formed of any desired material and is typically of the same material as the housing 2.

Now, the operation of the three-way cock 1 is described with reference to FIG. 4. On use, sections of tubing 12a, 12b and 12c are connected to the branches 4a, 4b and 4c of the housing 2, respectively.

When the lever 9 of the plug 5 is turned to the position shown by solid lines in FIG. 4, that is, in register with the branch 4c, the branch channels 40a and 40b come in flow communication via the channels 7b and 7c in the plug barrel 6 with the branch channel 40c sealed by the outer surface 60 of the plug barrel 6.

When the lever 9 of the plug 5 is turned to the position shown by phantom lines in FIG. 4, that is, in register with the branch 4b, the branch channels 40a and 40c come in flow communication via the channels 7a and 7c in the plug barrel 6 with the branch channel 40b sealed by the outer surface 60 of the plug barrel 6.

In one example where the section of tubing 12a is connected to a living body (not shown) side and the sections of tubing 12b and 12c connected to supply sources of two different medicaments (not shown), either one of the two medicaments can be selectively supplied to the living body by turning the lever 9 to either of the solid and phantom line positions in FIG. 4.

When the lever 9 of the plug 5 is turned to the position in register with the branch 4a (see FIG. 1), the branch channels 40b and 40c come in flow communication via the channels 7a and 7b in the plug barrel 6 with the branch channel 40a blocked by the outer surface 60 of the plug barrel 6.

The operator can manipulate the lever 9 to rotate the plug 5 without an error because he or she can see the marks 82a-82c and "OFF" indication 92. In addition, as previously described in conjunction with FIG. 1, the three-way cock 1 is designed such that the rotating restrainer 81 on the plug 5 comes in engagement with the stationary restrainer 32 on the housing 2 on either of opposite ends to restrain further movement of the plug 5 when the lever 9 is positioned in register with the branch 4a or 4c. Therefore, the operator can feel a physical engagement so that positioning operation is easy and accurate. Further, although the plug 5 is rotated against the friction between the outer surface 60 of barrel 6 and the inner surface of housing 2, such turning manipulation can be done by applying relatively small torques to the lever 9 because the barrel 6 is formed of a polyester elastomer.

EXAMPLE

Examples of the invention are given below by way of illustration and not by way of limitation.

Examples 1-12 and Comparative Examples 1-15

Three-way cocks of the above-illustrated structure were prepared. The diameter of barrel channel openings and the type and modulus in flexure of plug material were changed. The barrels of Examples 1-4, 5-8 and 9-12 were prepared from polyester elastomers while the barrels of Comparative Examples 1-5, 6-10 and 11-15 were prepared from comparative materials. The opening diameter, material, and modulus in flexure are shown in Tables 1 to 3.

The three-way cocks had the following specifications.

Housing:
Cylinder inner diameter: 8.4 mm
Branch channel diameter: 2.5 mm
Material: polycarbonate modulus in flexure $2.3 \times 10^4$ kgf/cm$^2$
Plug:
Barrel outer diameter: 8.6 mm
Barrel channel diameter: 2.5, 1.8 or 3.0 mm (=opening diameter)
Barrel material: reported in Tables 1-3

In each example, the cocks were examined for barrel channel edge scraping and air-tight seal as follows.

Scraping

First, the plug was inserted into the housing to complete a cock assembly. It was visually observed whether the barrel channels were scraped or chipped away at their opening edge. Next, the plug was rotated 200 back-and-forth strokes over 180 degrees. Another visual observation was made whether the barrel channels were scraped or chipped away at their opening edge.

Evaluation is based on the following criteria.
O: no scraping
Δ: some scraping
X: marked scraping

Air-tight seal

Three three-way cocks were connected as shown in FIG. 5. With the levers positioned as illustrated, the three cock arrangement was closed at one branch channel designated at X with a sealing member 13. Air under a pressure of 4 kgf/cm$^2$ was introduced through another branch channel designated at Y. The cocks were examined for air leakage to evaluate the tight seal against pressurized air. While the cock arrangement was dipped in water, bubble emergence was checked.

Evaluation is based on the following criteria.
A: no bubble emerged
B: some bubbles emerged
C: many bubbles emerged Air-tight seal was examined both after assembly and after heavy duty plug rotation as in the scraping test.

The results are shown in Tables 1 to 3.

As seen from the experimental data, the cocks of the present invention are well durable in that their plugs undergo no failure like scraping, chipping and abrasion during insertion of the plug into the housing and during repetitive plug changeovers.

Although some preferred embodiments have been described, many modifications and variations may be made thereto in the light of the above teachings. It is therefore to be understood that within the scope of the appended claims, the invention may be practiced otherwise than as specifically described.

TABLE 1

| | Channel opening diameter 2.5 mm | | | | | |
|---|---|---|---|---|---|---|
| | Plug material | | Scraping after | | Air-tight seal after | |
| Example | Type | Modulus in flexure (kgf/cm$^2$) | Assembled | Rotated | Assembled | Rotated |
| E1 | Perprene | 13,000 | O | O | A | A |
| E2 | Perprene | 5,000 | O | O | A | A |
| E3 | Perprene | 3,000 | O | O | A | A |
| E4 | Perprene | 1,000 | O | O | A | A |
| CE1 | Milastomer | 4,500 | Δ | Δ | B | B |
| CE2 | Milastomer | 3,200 | Δ | Δ | B | B |
| CE3 | High density PE | 12,500 | Δ | Δ | B | B |
| CE4 | Medium density PE | 6,500 | X | X | B | B |
| CE5 | Low density PE | 1,800 | X | X | C | C |

TABLE 2

| | Channel opening diameter 1.8 mm | | | | | |
|---|---|---|---|---|---|---|
| | Plug material | | Scraping after | | Air-tight seal after | |
| Example | Type | Modulus in flexure (kgf/cm$^2$) | Assembled | Rotated | Assembled | Rotated |
| E5 | Perprene | 13,000 | O | O | A | A |
| E6 | Perprene | 5,000 | O | O | A | A |
| E7 | Perprene | 3,000 | O | O | A | A |

TABLE 2-continued

Channel opening diameter 1.8 mm

| Example | Plug material Type | Modulus in flexure (kgf/cm²) | Scraping after Assembled | Scraping after Rotated | Air-tight seal after Assembled | Air-tight seal after Rotated |
|---|---|---|---|---|---|---|
| E8 | Perprene | 1,000 | ○ | ○ | A | A |
| CE6 | Milastomer | 4,500 | ○ | ○ | A | B |
| CE7 | Milastomer | 3,200 | ○ | ○ | A | B |
| CE8 | High density PE | 12,500 | ○ | ○ | A | B |
| CE9 | Medium density PE | 6,500 | ○ | △ | A | B |
| CE10 | Low density PE | 1,800 | △ | X | B· | C |

TABLE 3

Channel opening diameter 3.0 mm

| Example | Plug material Type | Modulus in flexure (kgf/cm²) | Scraping after Assembled | Scraping after Rotated | Air-tight seal after Assembled | Air-tight seal after Rotated |
|---|---|---|---|---|---|---|
| E9 | Perprene | 13,000 | ○ | ○ | A | A |
| E10 | Perprene | 5,000 | ○ | ○ | A | A |
| E11 | Perprene | 3,000 | ○ | ○ | A | A |
| E12 | Perprene | 1,000 | ○ | ○ | A | A |
| CE11 | Milastomer | 4,500 | △ | △ | B | B |
| CE12 | Milastomer | 3,200 | X | X | B | B |
| CE13 | High density PE | 12,500 | X | X | B | B |
| CE14 | Medium density PE | 6,500 | X | X | B | B |
| CE15 | Low density PE | 1,800 | X | X | C | C |

Perprene: trade mark of a polyether polyester elastomer by Toyobo K.K. surface hardness: Shore A 96 to 99
Milastomer: trade mark of an olefinic elastomer by Mitsui Petro-Chemical K.K.

I claim
1. A multi-way cock comprising
a housing including a cylindrical portion having a plurality of branch tubes extending from the outer periphery thereof, and
a plug including a barrel adapted to be rotatably fitted in the cylindrical portion of said housing and having a corresponding plurality of channels formed therein, said channels corresponding to said branch tubes in assembled condition, wherein said barrel is formed of a polyester elastomer having the formula:

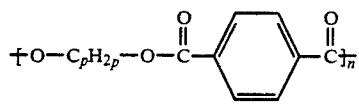

-continued

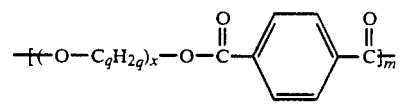

wherein n is a number ranging from 1 to 50, m is a number ranging from 1 to 5, p is a number ranging from 1 to 8, q is a number ranging from 1 to 8, and x is a number ranging from 5 to 50.

2. The cock of claim 1 wherein said polyester elastomer has a modulus in flexure of at least 800 kgf/cm².
3. The cock of claim 1 wherein said housing is formed of a rigid resin.
4. The cock of claim 1 wherein the openings that said channels define at the outer periphery of said barrel have a diameter of 1.5 to 5 mm.
5. The cock of claim 1 wherein said plug includes a lever for turning the plug in the housing, and the outer surface of said lever is entirely or partially coated with a resin which is different in color and/or appearance from the barrel-forming elastomer.
6. The cock of any one of claims 1 to 5 which is a three-way cock.
7. The cock of any one of claims 1 to 5 which is useful in the medical field.

* * * * *